United States Patent [19]

Lee et al.

[11] Patent Number: 5,189,058

[45] Date of Patent: Feb. 23, 1993

[54] IMINODICARBONIC, IMINODICARBONODITHIOIC, AND THIOCARBONYLCARBAMIC ACID ESTERS USEFUL AS ACAT INHIBITORS

[75] Inventors: Helen T. Lee, Ann Arbor; Joseph A. Picard; Drago R. Sliskovic, both of Ypsilanti, all of Mich.

[73] Assignee: Warner-Lambert Company, Morris Plains, N.J.

[21] Appl. No.: 683,208

[22] Filed: Apr. 9, 1991

[51] Int. Cl.$^5$ .................... A61K 31/27; C07C 333/00; C07C 261/00; C07C 69/76
[52] U.S. Cl. .................................. 514/481; 514/483; 558/233; 560/133; 560/135; 560/136; 560/137; 560/66
[58] Field of Search ............ 514/483, 481; 558/233; 560/133, 135, 136, 137, 66

[56] References Cited

U.S. PATENT DOCUMENTS

| | | | |
|---|---|---|---|
| 3,789,033 | 1/1974 | Hagemann et al. | 260/77.5 |
| 3,857,860 | 12/1974 | Kuhle et al. | 260/346.2 |
| 4,019,991 | 4/1977 | Jayne et al. | 55/235 |
| 4,348,331 | 9/1982 | Dickore et al. | 260/465 |
| 4,356,024 | 10/1982 | Dickore et al. | 71/93 |
| 4,386,101 | 5/1983 | Drabek et al. | 424/285 |
| 4,418,073 | 11/1993 | Maurer et al. | 424/273 |
| 4,447,635 | 5/1984 | Dickore et al. | 560/115 |
| 4,721,523 | 1/1988 | Schwamborn et al. | 71/93 |

FOREIGN PATENT DOCUMENTS 149019 11/1973 Czechoslovakia ............... 45/19
3409065 9/1985 Fed. Rep. of Germany ........ 251/16

OTHER PUBLICATIONS

CA 77:61917r, vol. 77, 1972.
*Chem. Zvesti,* 29(6):811–825 (1975), V. Konecny, "Synthesis and pesticidal activity of new derivatives of carbamic and thiocarbamic . . . ".

*Primary Examiner*—Mary C. Lee
*Assistant Examiner*—Robert C. Whittenbaugh
*Attorney, Agent, or Firm*—Ronald A. Daignault

[57] ABSTRACT

The compounds of the present invention have the formula

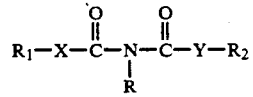

wherein each of X and Y is oxygen or sulfur, R is hydrogen or lower alkyl, and each of $R_1$ and $R_2$ is phenyl, substituted phenyl, naphthyl, substituted naphthyl, aralkyl, a hydrocarbon chain, a hetero group, or a heteroalkyl group, and the compounds are useful in treating atherosclerosis.

13 Claims, No Drawings

IMINODICARBONIC, IMINODICARBONODITHIOIC, AND THIOCARBONYLCARBAMIC ACID ESTERS USEFUL AS ACAT INHIBITORS

This invention relates to chemical compounds having pharmacological activity, to pharmaceutical compositions which include these compounds, and to a pharmaceutical method of treatment. More particularly, this invention concerns certain iminodicarbonic acid esters and iminodicarbonodithioic acid esters which inhibit the enzyme acyl coenzyme A:cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known cholesterol is transported in the blood in the form of complex particles consisting of a core of cholesteryl esters plus triglycerides and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides compounds of the following general Formula I, methods of using said compounds, and pharmaceutical compositions containing said compounds.

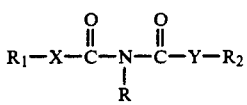

Formula I wherein each of X and Y is selected from oxygen or sulfur; wherein R is hydrogen or lower alkyl having from 1 to 4 carbon atoms; wherein each of $R_1$ and $R_2$ is selected from (a) phenyl which is unsubstituted or is substituted with from 1 to 3 substituents selected from
  phenyl,
  an alkyl group having from 1 to 6 carbon atoms and which is straight or branched,
  an alkoxy group having from 1 to 6 carbon atoms and which is straight or branched;
  phenoxy,
  hydroxy,
  fluorine,
  chlorine,
  bromine,
  $NO_2$,
  CN,
  trifluoromethyl,
  —COOH,
  —COOalkyl wherein alkyl has from 1 to 4 carbon atoms and is straight or branched,
  —$(CH_2)_p NR_3 R_4$ wherein p is zero or one, and each of $R_3$ and $R_4$ is selected from hydrogen or a straight or branched alkyl group having 1 to 4 carbon atoms;

(b) 1- or 2-naphthyl which is unsubstituted or is substituted with from 1 to 3 substituents selected from
  phenyl,
  an alkyl group having from 1 to 6 carbon atoms and which is straight or branched,
  an alkoxy group having from 1 to 6 carbon atoms and which is straight or branched;
  hydroxy,
  phenoxy,
  fluorine,
  chlorine,
  bromine,
  nitro,
  CN,
  trifluoromethyl,
  —COOH,
  —COOalkyl wherein alkyl has from 1 to 4 carbon atoms and is straight or branched,
  —$(CH_2)_p NR_3 R_4$ wherein p, $R_3$ and $R_4$ have the meanings defined above;

(c) the group

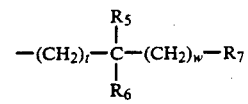

wherein t is zero or 1 to 4; w is zero or 1 to 4 with the proviso that the sum of t and w is not greater than 5; $R_5$ and $R_6$ are independently selected from hydrogen or alkyl having from 1 to 6 carbon atoms, or when $R_5$ is hydrogen, $R_6$ can be selected from —COOalkyl wherein alkyl has from 1 to 4 carbon atoms or the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_p NR_3 R_4$ wherein P, $R_3$ and $R_4$ have the meanings defined above;

(d) —(CH$_2$)$_s$—Q wherein s is a number of from 0 to 3 and Q is a 5- or 6 membered monocyclic heterocycle containing 1 or 2 nitrogen, oxygen or sulfur atoms;

(e) a straight or branched hydrocarbon chain having from 1 to 20 carbon atoms and which is saturated or contains from 1 to 3 double bonds; and pharmaceutically acceptable salts thereof with the proviso that one of R$_1$ or R$_2$ is phenyl or substituted phenyl.

DETAILED DESCRIPTION OF INVENTION

The compound of general Formula I are ACAT inhibitors, rendering them useful in treating hypercholesterolemia and atherosclerosis. The compounds of general Formula I are (a) iminodicarbonic acid esters wherein each of X and Y is oxygen, are (b) iminodicarbonodithioic acid esters wherein each of X and Y is sulfur or are (c) thiocarbonylcarbamic acid esters wherein one of X and Y is oxygen and the other of X and Y is sulfur and can be depicted respectively as follows:

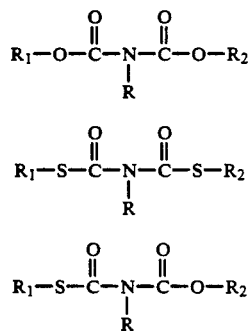

In Formulas (a), (b), and (c), R, R$_1$, and R$_2$ have the meanings defined in Formula I.

In general Formula I illustrative examples of straight or branched saturated hydrocarbon chains having from 1 to 20 carbon atoms include methyl, ethyl, n-propyl, isopropyl, n-butyl, iso-butyl, tert-butyl, n-pentyl, iso-pentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, tert-butoxy, and pentyloxy.

Illustrative examples of straight or branched alkyl groups having from 1 to 6 carbon atoms are as used in Formulas I and II include methyl, ethyl, n-propyl, isopropyl, n-pentyl, n-butyl, and tert-butyl.

A 5- or 6-membered monocyclic heterocycle is an aromatic ring containing 1 or 2 nitrogen, oxygen, or sulfur atoms or a combination thereof. Such a heterocyclic group includes, for example, thienyl, furanyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, indolyl, or N-oxides of heterocycles containing a nitrogen atom.

More specifically, such a heterocycle may be a 2- or 3-thienyl; 2- or 3-furanyl; 2-, or 3-, or 4-pyridyl or -pyridyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-oxazolyl; 2-, 4-, or 5-thiazolyl, 3-, 4-, or 5-isoxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; or 2-, 3-, 4-, 5-, 6-, or 7-indolyl.

Pharmaceutically acceptable salts of the compounds of Formulas I and II are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J. Pharm. Sci. 66, 1–19 (1977).

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Preferred compounds of the present invention are those wherein one of R$_1$ and R$_2$ is phenyl, and more preferably phenyl disubstituted in the 2,6-positions.

More preferred are compounds wherein one of R$_1$ and R$_2$ is phenyl or disubstituted phenyl and the other of R$_1$ and R$_2$ is phenyl or disubstituted phenyl or is a straight or branched hydrocarbon chain having from 1 to 20 carbon atoms and is saturated or contains from 1 to 3 double bonds.

Most preferably, one of R$_1$ and R$_2$ is phenyl disubstituted in the 2,6-positions, and the other of R$_1$ and R$_2$ is a saturated straight or branched hydrocarbon chain having from 1 to 20 carbon atoms or is phenyl disubstituted in the 2,6-positions.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica* 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed in $IC_{50}$ values; i.e., the concentration of test compound required to inhibit the activity of the enzyme by 50%.

TABLE 1

| Compound of Example | $IC_{50}$ ($\mu M$) |
| --- | --- |
| 1 | 0.35 |
| 2 | 0.021 |
| 3 | 0.017 |
| 4 | 0.021 |
| 5 | 0.064 |
| 6 | 0.093 |
| 7 | 0.098 |
| 8 | 0.129 |
| 9 | 0.102 |
| 10 | 0.05 |
| 11 | 0.14 |
| 12 | 1.2 |
| 13 | 0.098 |
| 14 | 0.27 |
| 15 | 0.049 |
| 16 | 0.25 |
| 17 | 0.074 |
| 18 | 0.028 |
| 24 | 0.11 |
| 25 | 0.94 |
| 26 | 1.2 |
| 27 | 3.7 |
| 28 | 1.8 |
| 29 | >5 |
| 30 | >5 |
| 31 | >1 |
| 32 | 10.371 |
| 33 | 0.23 |
| 34 | >5 |
| 36 | >5 |
| 37 | 0.6 |

In one in vivo screen designated APCC, male Sprague-Dawley rats (200 to 225 g) were randomly divided into treatment groups and dosed at 4 PM with either vehicle (CMC/Tween) or suspensions of compounds in vehicle at a dose of 30 mg/kg. The normal chow diet was then replaced with a high fat, high cholesterol diet (designated PCC) containing 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Compound of Example | % Change (mg/dl) |
| --- | --- |
| 1 | −13 |
| 2 | −52 |
| 3 | −50 |
| 4 | −51 |
| 5 | −29 |
| 6 | −38 |
| 7 | −25 |
| 8 | −49 |
| 9 | −60 |
| 10 | −70 |
| 11 | −65 |
| 12 | −34 |
| 13 | −56 |
| 14 | −54 |
| 15 | −66 |
| 16 | −47 |
| 17 | −43 |
| 18 | −63 |
| 19 | −20 |
| 20 | −52 |
| 24 | −43 |
| 25 | −12 |
| 26 | −11 |
| 28 | −19 |
| 30 | −15 |
| 31 | −35 |
| 32 | −36 |
| 33 | −33 |
| 35 | −4 |
| 37 | −8 |

In therapeutic use as agents for treating hypercholesterolemia or atherosclerosis, the compounds of Formulas I or II or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention wherein R is hydrogen are prepared as set below wherein $R_1$, $R_2$, X, and Y have the meanings defined in Formula I.

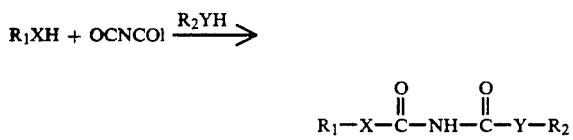

A solution of the alcohol or thiol, $R_1XH$, in an appropriate solvent such as diethyl ether, tetrahydrofuran, or dichloromethane is added dropwise to a cold (<0° C.) solution of chlorocarbonyl isocyanate in a similar solvent. The resulting solution is aged (0.5 to 6 hours) before a solution of a second alcohol or thiol $R_2YH$ and an acid scavenger such as triethylamine or pyridine in an appropriate solvent, such as diethyl ether tetrahydrofuran or dichloromethane, is added dropwise. The reaction is then warmed to room temperature and aged (0.5 to 16 hours). The reaction is partitioned between an appropriate organic solvent and an aqueous acid solution. The organic solution is dried with a drying agent such as magnesium sulfate or sodium sulfate then concentrated to give a crude product mixture. Chromatography of the mixture gives the desired product.

Compounds of Formula I wherein R is lower alkyl are prepared from the corresponding compounds wherein R is hydrogen by treatment with DBU (1,8-diazabicyclo[5.4.0]undec-7-ene) and an alkyliodide by procedures well known in the art.

The alcohols and thiols, $R_1XH$ and $R_2YH$, used in preparing the compounds of the present invention are commercially available or are prepared by means readily known in the art.

The following specific examples further illustrate the preparation of compounds of this invention.

EXAMPLE 1

Iminodicarbonic acid, 2,6-bis(1-methylethyl)phenyldiphenylmethyl ester

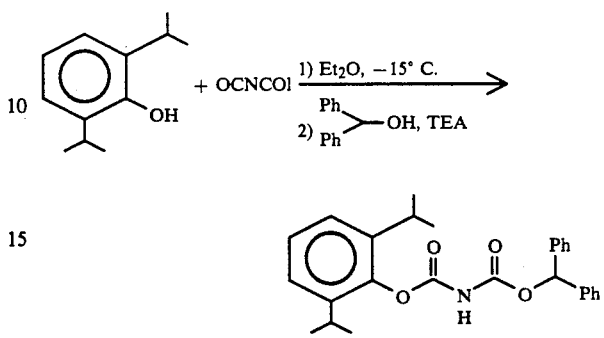

A solution of 2,6-diisopropyl phenol (1.45 g, 8.1 mmol) in 30 mL $Et_2O$ was added dropwise to a solution of chlorocarbonyl isocyanate (0.66 mL, 8.1 mmol) in 30 mL $Et_2O$ at −15° C. The reaction was stirred for 45 minutes before a solution of benzhydrol (1.5 g, 8.1 mmol) and excess triethylamine (~1.0 mL) in 50 mL $Et_2O$ was added dropwise. The resulting mixture was warmed to room temperature for 1 hour and then partitioned between 1N HCl and EtOAc. The organic layer was dried over $MgSO_4$, filtered, and evaporated to give a yellow oil. Chromatography gave the title compound (1.0 g, 29%) as a white solid.

When in the procedure of Example 1 an appropriate amount of the alcohol or thiol listed below is substituted for benzhydrol and the general procedure of Example 1 was followed, the respective products listed below were obtained.

| Example Number | Alcohol/Thiol | Product |
|---|---|---|
| 2 | dodecanol | Iminodicarbonic acid, dodecyl 2,6-bis(1-methylethyl)phenyl ester, m.p. 60–62° C. |
| 3 | 1-methyltridecanol | Iminodicarbonic acid, 2,6-bis(1-methylethyl)phenyl 1-methyltridecyl ester, (±), m.p. 55–57° C. |
| 4 | 1,1-dimethyltridecanol | Iminodicarbonic acid, 2,6-bis(1-methylethyl)phenyl 1,1-dimethyltridecyl ester; $^1$H NMR: 7.1–7.28δ (m, 4H), 2.9–3.1(m, 2H), 1.54(s, 6H), 1.1–1.55(m, 34H), 0.89(t, 3H), 1.72–1.9 (m, 2H)ppm |
| 5 | 1,1-dimethylpentanol | Iminodicarbonic acid, 2,6-bis(1-methylethyl)phenyl 1,1-dimethylpentyl ester, m.p. 95–97° C. |
| 6 | hexanol | Iminodicarbonic acid, 2,6-bis(1-methylethyl)phenyl hexyl ester, m.p. 53–55° C. |
| 7 | (S)-1-methylhexanol | Iminodicarbonic acid, 2,6-bis(1-methylethyl)phenyl 1-methylhexyl ester (S), m.p. 124–128° C. |
| 8 | (R)-1-methylhexanol | Iminodicarbonic acid, 2,6-bis(1-methylethyl)phenyl 1-methylhexyl ester (R), m.p. 68–70° C. |
| 9 | 1-methylhexanol | Iminodicarbonic acid, 2,6-bis(1-methylethyl)- |

-continued

| Example Number | Alcohol/Thiol | Product |
|---|---|---|
| | | phenyl 1-methylhexyl ester, (±), m.p. 58–60° C. |
| 10 | hexadecanol | Iminodicarbonic acid, 2,6-bis(1-methylethyl)phenyl hexadecyl ester, m.p. 73–75° C. |
| 11 | undecanol | Iminodicarbonic acid, 2,6-bis(1-methylethyl)phenyl undecyl ester, m.p. 55–57° C. |
| 12 | octadecanol | Iminodicarbonic acid, 2,6-bis(1-methylethyl)phenyl octadecyl ester, m.p. 73–75° C. |
| 13 | 1-methyloctanol | Iminodicarbonic acid, 2,6-bis(1-methylethyl)phenyl 1-methyloctadecyl ester, $^1$H NMR: 7.15–7.29(m, 3H), 2.85–3.0(m, 2H), 4.29–4.9 (m, 1H) 0.86, (t, 3H), 1.1–1.7(m, 27H)ppm |
| 14 | 1-methylnonanol | Iminodicarbonic acid, 2,6-bis(1-methylethyl)phenyl 1-methylnonyl ester, m.p. 41–44° C. |
| 15 | 1-methylundecanol | Iminodicarbonic acid, 2,6-bis(1-methylethyl)phenyl 1-methylundecyl ester, m.p. 50–52° C. |
| 16 | octanol | Iminodicarbonic acid, 2,6-bis(1-methylethyl)phenyl octyl ester, $^1$H NMR: 7.1–7.35(m, 4H), 4.25(t, 2H), 2.9–3.1(m, 2H), 1.1–1.85(m, 24H), 0.87(t, 3H)ppm |
| 17 | decanol | Iminodicarbonic acid, 2,6-bis(1-methylethyl)phenyl decyl ester, m.p. 45–47° C. |
| 18 | dodecylthiol | [(Dodecylthio)carbonyl]carbamic acid, 2,6-bis(1-methylethyl)phenyl ester, m.p. 55–57° C. |
| 19 | 2,6-bis[(1-methylethyl)phenyl]thiol | 2,6-Bis[[(1-methylethyl)phenyl]thio]carbamic acid, 2,6-bis(1-methylethyl)phenyl ester, m.p. 160–164° C. |
| 20 | decylthiol | [(Decylthio)carbonyl]carbamic acid, 2,6-bis(1-methylethyl)phenyl ester, m.p. 50–52° C. |
| 21 | 2-furanylmethylthiol | [(2-Furanylmethylthio)carbonyl]carbamic acid, 2,6-bis(1-methylethyl)phenyl ester, m.p. 121–123° C. |
| 22 | 3-phenylpropylthiol | [(3-Phenylpropylthio)carbonyl]carbamic acid, 2,6-bis(1-methylethyl)phenyl ester, 102–105° C. |
| 23 | 4-chlorobenzylthiol | [(4-Chlorobenzylthio)carbonyl]carbamic acid, 2,6-bis(1-methylethyl)phenyl ester, m.p. 115–117° C. |
| 24 | 2,6-bis(1-methylethyl)phenol | Iminodicarbonic acid, di[2,6-bis(1-methylethyl)phenyl]ester, m.p. 152–153.5° C. |
| 25 | α-hydroxybenzeneacetic acid, methyl ester | α-[[[[[2,6-Bis(1-methylethyl)phenoxy]carbonyl]amino]carbonyl]oxy]benzeneacetic acid, methyl ester, m.p. 130–134° C. |
| 26 | 1-naphthol | Iminodicarbonic acid, [2,6-bis(1-methylethyl)phenyl](1-naphthalenyl) ester, m.p. 152–154° C. |
| 27 | phenol | Iminodicarbonic acid, 2,6-bis(1-methylethyl)phenyl phenyl ester, |

| Example Number | Alcohol/Thiol | Product |
|---|---|---|
| | | m.p. 144–147° C. |
| 28 | phenylthiol | [(Phenylthio)carbonyl]carbamic acid, 2,6-bis(1-methylethyl)phenyl]ester, m.p. 150–152° C. |

When in the procedure of Example 1 an appropriate amount of the alcohols or thiols listed below are substituted for 2,6-diisopropylphenol and benzhydrol and the general procedure of Example 1 is followed, the respective products listed below were obtained.

| Example Number | Alcohol/Thiol | Product |
|---|---|---|
| 29 | 2,4,6-trimethoxyphenol and dodecanol | Iminodicarbonic acid, dodecyl 2,4,6-trimethoxyphenyl ester, m.p. 87–89° C. |
| 30 | 2,4-difluorophenol and 1-methyltridecanol | Iminodicarbonic acid, 2,4-difluorophenyl 1-methyltridecyl ester, m.p. 65–67° C. |
| 31 | 2,6-diisopropylphenylthiol and dodecanthiol | Iminodicarbonodithioic acid, 5-[2,6-bis(1-methylethyl)phenyl] S'-dodecyl ester, m.p. 50–52° C. |
| 32 | 2,6-diphenylphenol and 2,6-diphenylphenol | Iminodicarbonic acid, di[1,1'[3',1''-terphenyl]-2-yl]ester, m.p. >275° C. |
| 33 | 2,6-dimethylphenylthiol and 2,6-dimethylphenylthiol | Iminodicarbonodithioic acid, S,S'-bis[2,6-bis(methyl)phenyl]ester, m.p. 218–222° C. |
| 34 | 2,6-diisopropylphenylthiol and dodecanol | [[[2,6-Bis(1-methylethyl)phenyl]thio]carbonyl]carbamic acid, dodecyl ester, m.p. 115–119° C. |
| 35 | 2,6-bis(tert-butyl)phenol and 2,6-bis(tert-butyl)phenol | Iminodicarbonic acid bis[2,6-bis(1,1-dimethylethyl)phenyl]ester, m.p. 195–197° C. |

EXAMPLE 36

Iminodicarbonic acid, di(diphenylmethyl)ester

When in the procedure of Example 1 an appropriate amount of benzhydrol was substituted for 2,6-diisopropylphenol, the title compound was obtained, m.p. 141°–146° C.

EXAMPLE 37

Methyliminodicarbonic, 2,6-bis(1-methylethyl)phenyl 1-methyltridecyl ester

DBU (10.7 mmol, 1.6 mL) was added dropwise to a mixture of the compound of Example 3 (9.7 mmol, 4.47 g) and MeI (10.7 mmol, 1.52 g) in 100 mL of CH$_3$CN at −15° C. The resulting mixture was stirred at room temperature overnight. The solvent was evaporated under vacuum and the residue was partitioned between 20 mL of dilute HCl and 20 mL EtOAc. The organic layer was separated, dried over MgSO$_4$, and evaporated. The product was isolated by chromatography (hexane:CH$_2$Cl$_2$=4:1). The clear oil weighed 3.48 g (75%); $^1$H NMR 7.1–7.23 (m, 3H), 4.95–5.1 (m, 1H), 3.39 (s, 3H), 2.95–3.1 (m, 2H), 0.87–1.7 (m, 40H) ppm.

We claim:

1. A compound of the formula

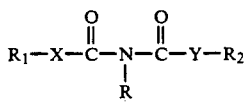

wherein each of X and Y is oxygen or sulfur; wherein R is hydrogen or alkyl having from 1 to 4 carbon atoms; wherein $R_1$ is phenyl disubstituted on the 2- and 6-positions with groups selected from an alkyl group having from 1 to 6 carbon atoms and which is straight or branched; an alkoxy group having from 1 to 6 carbon atoms and which is straight or branched; phenoxy, hydroxy, fluorine, chlorine, bromine, $NO_2$, CN, trifluoromethyl, —COOH, —COOalkyl wherein alkyl has from 1 to 4 carbon atoms and is straight or branched, —$(CH_2)_p$—$NR_3R_4$ wherein p is zero or one, and each of $R_3$ and $R_4$ is selected from hydrogen or a straight or branched alkyl group having from 1 to 4 carbon atoms; wherein $R_2$ is selected from (a) phenyl which is unsubstituted or is substituted with from 1 to 3 substituents selected from
phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
$NO_2$,
CN,
trifluoromethyl,
—COOH,
—COOalkyl wherein alkyl has from 1 to 4 carbon atoms and is straight or branched,
—$(CH_2)_pNR_3R_4$ wherein p, $R_3$, and $R_4$ have the meanings defined above, (b) 1- or 2-naphthyl which is unsubstituted or is substituted with from 1 to 3 substituents selected from
phenyl,
an alkyl group having from 1 to 6 carbon atoms and which is straight or branched,
an alkoxy group having from 1 to 6 carbon atoms and which is straight or branched;
hydroxy,
phenoxy,
fluorine,
chlorine,
bromine,
nitro,
CN,
trifluoromethyl,
—COOH,
—COOalkyl wherein alkyl has from 1 to 4 carbon atoms and is straight or branched,
—$(CH_2)_pNR_3R_4$ wherein p, $R_3$ and $R_4$ have the meanings defined above;

(c) the group

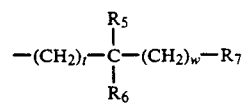

wherein t is zero or 1 to 4; w is zero or 1 to 4 with the proviso that the sum of t and w is not greater than 5; $R_5$ and $R_6$ are independently selected from hydrogen or alkyl having from 1 to 6 carbon atoms, or when $R_5$ is hydrogen, $R_6$ is —COOalkyl wherein alkyl has from 1 to 4 carbon atoms or can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_pNR_3R_4$ wherein P, $R_3$ and $R_4$ have the meanings defined above; or (d) a straight or branched hydrocarbon chain having from 1 to 20 carbon atoms and which is saturated or contains from 1 to 3 double bonds; and pharmaceutically acceptable salts thereof.

2. A compound of claim 1 wherein $R_2$ is a straight or branched hydrocarbon chain having from 1 to 20 carbon atoms and which is saturated or contains from 1 to 3 double bonds.

3. A compound of claim 1 wherein $R_2$ is phenyl or substituted phenyl.

4. A compound of claim 1 wherein each of X and Y is oxygen.

5. A compound of claim 1 wherein each of X and Y is sulfur.

6. A compound of claim 1 wherein one of X and Y is oxygen and the other of X and Y is sulfur.

7. A compound of claim 1 wherein $R_1$ is 2,6-bis(1-methylethyl)phenyl, X and Y are oxygen, and $R_2$ is a saturated hydrocarbon chain and is straight or branched.

8. A compound of claim 7 which is
Iminodicarbonic acid, dodecyl 2,6-bis(1-methylethyl)phenyl ester,
Iminodicarbonic acid, 2,6-bis(1-methylethyl)phenyl 1-methyltridecyl ester,
Iminodicarbonic acid, 2,6-bis(1-methylethyl)phenyl 1,1-dimethyltridecyl ester;
Iminodicarbonic acid, 2,6-bis(1-methylethyl)phenyl 1,1-dimethylpentyl ester,
Iminodicarbonic acid, 2,6-bis(1-methylethyl)phenyl hexyl ester,
Iminodicarbonic acid, 2,6-bis(1-methylethyl)phenyl 1-methylhexyl ester (S),
Iminodicarbonic acid, 2,6-bis(1-methylethyl)phenyl 1-methylhexyl ester (R),
Iminodicarbonic acid, 2,6-bis(1-methylethyl)phenyl 1-methylhexyl ester, (±),
Iminodicarbonic acid, 2,6-bis(1-methylethyl)phenyl hexadecyl ester,
Iminodicarbonic acid, 2,6-bis(1-methylethyl)phenyl undecyl ester,
Iminodicarbonic acid, 2,6-bis(1-methylethyl)phenyl octadecyl ester,
Iminodicarbonic acid, 2,6-bis(1-methylethyl)phenyl 1-methyloctadecyl ester, Iminodicarbonic acid, 2,6-bis(1-methylethyl)phenyl 1-methylnonyl ester, Iminodicarbonic acid, 2,6-bis(1-methylethyl)phenyl 1-methylundecyl ester, Iminodicarbonic acid, 2,6-bis(1-methylethyl)phenyl octyl ester, Iminodicarbonic acid, 2,6-bis(1-methylethyl)phenyl decyl ester, and Methyliminodicarbonic, 2,6-bis(1-methylethyl)phenyl 1-methyltridecyl ester.

9. A compound of claim 1 wherein $R_1$ is 2,6-bis(1-methylethyl)phenyl, X is oxygen, and Y is sulfur.

10. A compound of claim 9 which is
[(Dodecylthio)carbonyl]carbamic acid, 2,6-bis(1-methylethyl)phenyl ester,
2,6-Bis[[(1-methylethyl)phenyl]thio]carbamic acid, 2,6-bis(1-methylethyl)phenyl ester,
[(Decylthio)carbonyl]carbamic acid, 2,6-bis(1-methylethyl)phenyl ester,
[(3-Phenylpropylthio)carbonyl]carbamic acid, 2,6-bis(1-methylethyl)phenyl ester,
[(4-Chlorobenzylthio)carbonyl]carbamic acid, 2,6-bis(1-methylethyl)phenyl ester, and
[(Phenylthio)carbonyl]carbamic acid, 2,6-bis(1-methylethyl)phenyl]ester.

11. A compound of claim 1 which is
Iminodicarbonic acid, 2,6-bis(1-methylethyl)phenyl-diphenylmethyl ester,
[[[2,6-Bis(1-methylethyl)phenyl]thio]carbonyl]carbamic acid, dodecyl ester,
Iminodicarbonodithioic acid, 5-[2,6-bis(1-methylethyl)phenyl]S'-dodecyl ester,
Iminodicarbonic acid, di[2,6-bis(1-methylethyl)phenyl]ester,
α-[[[[[2,6-Bis(1-methyl-ethyl)phenoxy]carbonyl]amino]carbonyl]oxy]benzeneacetic acid, methyl ester,
Iminodicarbonic acid, bis[2,6-bis(1,1-dimethylethyl)phenyl]ester,
Iminodicarbonic acid, [2,6-bis(1-methylethyl)phenyl](1-naphthalenyl) ester,
Iminodicarbonic acid, di[1,1'[3',1''-terphenyl]-2-yl]ester,
Iminodicarbonic acid, 2,6-bis(1-methylethyl)phenyl phenyl ester,
[(Phenylthio)carbonyl]carbamic acid, 2,6-bis(1-methylethyl)phenyl]ester, and
Iminodicarbonodithioic acid, S,S'-bis[2,6-bis(methyl)phenyl]ester.

12. A pharmaceutical composition which comprises a compound of claim 1 and a pharmaceutically acceptable carrier.

13. A method of treating hypercholesterolemia and atherosclerosis which comprises administering to a patient in need thereof an effective amount of a compound of claim 1.

* * * * *